United States Patent [19]

Nakagawa et al.

[11] Patent Number: 4,959,469

[45] Date of Patent: Sep. 25, 1990

[54] CRYSTALLINE CEPHALOSPORIN COMPOUNDS

[75] Inventors: Susumu Nakagawa; Ryosuke Ushijima; Fumio Nakano; Koji Yamada, all of Okazaki; Eiichi Mano, Kariya, all of Japan

[73] Assignee: Banyu Pharmaceutical Company, Ltd., Tokyo, Japan

[21] Appl. No.: 315,917

[22] Filed: Feb. 27, 1989

Related U.S. Application Data

[63] Continuation of Ser. No. 813,614, Dec. 26, 1985, Pat. No. 4,677,100.

[30] Foreign Application Priority Data

Dec. 27, 1984 [JP] Japan ............................. 59-273591
Aug. 6, 1985 [JP] Japan ............................. 60-171839
Dec. 9, 1986 [JP] Japan ............................. 61-291431
Jun. 25, 1987 [WO] PCT Int'l Appl. ... PCT/JP87/00417

[51] Int. Cl.$^5$ ............................................ C07D 501/46
[52] U.S. Cl. ..................................... 540/222; 540/225
[58] Field of Search ................. 540/222, 225; 514/202

[56] References Cited

U.S. PATENT DOCUMENTS

4,677,100 6/1987 Nakagawa et al. ................ 540/222

FOREIGN PATENT DOCUMENTS

60-13793 1/1985 Japan .
61-215689 10/1985 Japan .
61-267587 11/1986 Japan .
62-103090 5/1987 Japan .

OTHER PUBLICATIONS

The Merch Body, pp. 268, 269 and 270, Tenth Edition, (1983).

Primary Examiner—Nicholas S. Rizzo
Attorney, Agent, or Firm—Oblon, Spivak, McClelland, Maier & Neustadt

[57] ABSTRACT

The present invention relates to stable cyrstalline (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)-3-cephem-4-carboxylate sulfate or its hydrate, a process for production of the compound and (6R,7R)-7-[(Z)-2-(2-aminothiazol-4-yl)-2-(1-carboxyl-1-methylethoxyimino)acetamido]-3-(5,6-dihydroxy-2-methyl-2-isoindolinium)methyl-3-cephem-4-carboxylate hydrochloride or its hydrate which is a starting material useful for the production of the desired compound of the present invention.

3 Claims, No Drawings

CRYSTALLINE CEPHALOSPORIN COMPOUNDS

This application is a continuation-in-part of parent application Ser. No. 06/813,614, filed Dec. 26, 1985, now U.S. Pat. No. 4,677,100, patented June 30, 1987.

TECHNICAL FIELD

The present invention relates to cephalosporin compounds useful in the medicinal field as medicines for curing infectious disease caused by bacteria, more specifically, crystalline (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrates, a process for producing the compounds and intermediates of the compounds. Further, the present invention relates to (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate hydrochloride or its hydrates.

efficiently. The present invention has been accomplished on the basis of these discoveries.

DISCLOSURE OF INVENTION

The present invention relates to stable crystalline sulfate of (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate, a process for producing the compound and intermediates of the compound. Further, the present invention relates to (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate hydrochloride or its hydrate useful as the starting material.

Here, the (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate is shown by the following chemical formula:

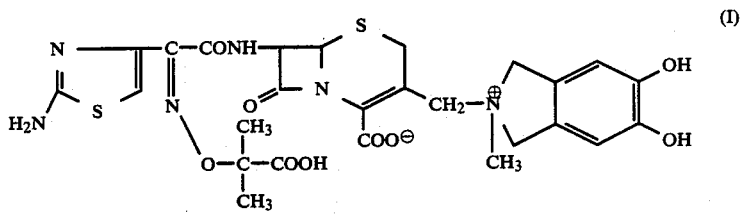

BACKGROUND ART (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate is a compound for which the present inventors filed an application for patent and which was disclosed in Japanese Unexamined Patent Publication No. 267587/1986. It exhibits excellent antibacterial activities against Gram-negative bacteria, particularly glucose non-fermentative Gram-negative rods, for example, *Pseudomonas aeruginosa*, *Pseudomonas cepacia*, *Pseudomonas maltophilia* and *Acinetobacter calcoaceticus*, and further, exhibits strong antibacterial activities against *Pseudomonas aeruginosa* AKR17 which resists known cephalosporin antibiotics. Thus, it is a prospective compound practically useful as a medicine for curing infectious diseases caused by bacteria.

The present inventors have found that the sulfate of (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate or its crystalline hydrate is more stable than the non-crystalline powder of the compound. The have conducted further researches based on this discovery, and have also found that in the process for its production,
(6R,7R)-7-[(Z)-2-(2-aminothiazol-4-yl)-2-(1-carboxy--1methylethoxyimino)acetamido]-3-(5,6-dihydroxy-2-methyl-2-isoindolinium)methyl-3-cephem-4-carboxylate is made into a crude hydrochloride thereof or a hydrate of the hydrochloride, followed by conversion to a sulfate thereof or a hydrate of the sulfate, whereby the (6R,7R)7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate can be isolated and purified and will hereinafter be referred to simply as the compound I.

Now, the process for producing the desired compound will be described in detail.

The crystalline sulfate of the compound I or its hydrate which is the desired compound of the present invention, can be produced by dissolving the compound I in its free form, its acid addition salt, hydrate or non-crystalline powder, or a crude product thereof in water, a hydrophilic organic solvent or a water-containing hydrophilic organic solvent, if necessary, by adding an acid or a base, followed by addition of sulfuric acid and, if necessary, water.

Here, the acid addition salt of the compound I, its hydrate or non-crystalline powder, or a crude product thereof, as the starting material of the present invention, can be prepared by the process disclosed in Example 1 or Reference Example 1 as mentioned below, or a process similar to such a process. As the acid addition salt of the compound I among the starting materials of the present invention, there may be mentioned, for example, a hydrochloride, hydrobromide, phosphate, sulfate, nitrate or trifluoroacetate. Particularly, the hydrochloride or its hydrate is preferred in view of the easiness in handling during the production and the good yield.

The starting material of the present invention is added to a lower alkylalcohol such as methanol, ethanol, propanol, isopropanol or butanol, a hydrophilic organic solvent such as tetrahydrofuran, acetonitrile, propionitrile or acetone, water, or a hydrophilic organic solvent containing from 10 to 90% of water, at a temperature of from 5° to −10° C., and from 1 to 6N sulfuric acid and, if necessary, water are added thereto at the same temperature whereby the crystals of the compound I precipitate. The crystals are separated by filtration and then dried in air under a suitable condition, for example at a temperature of from 5° to 25° C.

or under reduced pressure at a temperature of from −20° to 25° C. to obtain crystals of the desired compound of the present invention i.e. the sulfate of the compound I or its hydrate.

As the hydrate of the desired compound of the present invention, a hydrate having from 1 to 10 water molecules may be mentioned, for example, a monohydrate, tetrahydrate, pentahydrate, hexahydrate, heptahydrate or octahydrate of the compound I.

Now, when the desired compound of the present invention is used as a medicine, it is available in the form of the following formulations.

The compound of the present invention may be mixed with solid or liquid excipient, and may be used in the form of a pharmaceutical formulation suitable for oral administration, parenteral administration or external administration. As the pharmaceutical formulations, there may be mentioned liquid formulations such as injection solutions, syrups and emulsions, solid formulations such as tablets, capsules and granules, and formulations for external application such as ointments and suppositories.

The above-mentioned formulations may contain commonly used additives such as bases, assisting agents, stabilizers, wetting agents or emulsifying agents. For instance, as the base, $NaHCO_3$, $KHCO_3$, $Na_2CO_3$ or $K_2CO_3$ may be used. For injection solutions, there may be used a solubilizing liquid for injection such as distilled water, a physiological sodium chloride aqueous solution or a Ringer solution and a preservative such as methyl p-hydroxybenzoate or propyl p-hydroxybenzoate. For liquid agents such as syrups and emulsions, there may be used an emulsifying agents such as gum arabic, gelatin or lecithin and surfactant such as Tween® or Span® in addition to sorbitol syrup, methyl cellulose, glucose, sucrose syrup, gelatin, hydroxyethyl cellulose, carboxymethyl cellulose, aluminum stearate gel, an edible oil, almond oil, coconut oil, oil ester, sorbitan monooleate, propylene glycol, glycerin, ethyl alcohol or water. For a solid formulation, lactose, sucrose, corn starch, calcium phosphate, magnesium stearate, talc, silicic acid, gum arabic, gelatin, sorbitol, traganto, polyvinylpyrrolidone, polyethylene glycol or sodium lauryl sulfate, may be employed. As the base material for ointments or suppositories, there may be employed, for instance, cacao butter, glycerides, polyethylene glycols, white vaseline, etc. A surfactant or a absorption accelerating agent may be incorporated, as the case requires.

The desired compound of the present invention may be employed for the treatment and prevention of diseases caused by bacterial infections, such as infectious diseases of the respiratory system, infectiousness of the genito-urinary tract, infectious diseases of pregnant women, suppurative diseases or surgical infectious diseases. The dose may vary depending upon the age and the condition of the patient, and is usually from 1 to 135 mg/kg per day. It is preferred to administer a daily dose of from 5 to 35 mg/kg in 2 to 4 times.

Now, the present invention will be described in further detail with reference to Examples and Reference Examples. However, it should be understood that the present invention is by no means restricted to these specific Examples.

Experiment: Stability test

Each 10 mg of the crystalline powder of the sulfate of the compound I prepared by the process of the present invention i.e. the process of Example 3, and the amorphous powder of the compound I, was sealed in a vial, and then, stored at 25° C. One month later from the beginning of the storage, the residual rates (%) were determined by high performance liquid chromatography (HPLC). The results are shown in the following table.

| Sample | Residual rate % |
|---|---|
| Crystals of the sulfate of the compound I (the compound of the present invention) | 99.2 |
| Amorphous powder of the compound I | 90.2 |

As is evident from the above table, as compared with the amorphous powder, the compound of the present invention has excellent storage stability and a low reducing rate of the content. Thus, the compound of the present invention is superior as a curing agent for infectious diseases caused by bacteria.

EXAMPLE

EXAMPLE 1

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate hydrochloride 153.3 ml (1.43 mol) of phosphorus oxychloride and 110.7 ml (1.43 mol) of N,N-dimethylformamide were added to 2 l of ethyl acetate under stirring, and the mixture was stirred at room temperature for 20 minutes. 11 l of ethyl acetate was added thereto, and the mixture was cooled to a temperature of at most 0° C. 743.2 g (1.3 mol) of (Z)-2-(1-tert-butoxycarbonyl-1-methylethoxyimino)- 2-(2-tritylaminothiazol-4-yl)acetic acid was added thereto, and the mixture was stirred at room temperature for 30 minutes. The reaction solution was cooled to a temperature of at most −10° C., 526.9 g (1.3 mol) of p-methoxybenzyl (6R,7R)-7-amino-3-chloromethyl-3-cephem-4-carboxylate hydrochloride was added thereto, and 453.3 ml (3.25 mol) of triethylamine was dropwise added thereto at a temperature of at most −5° C. over a period of 30 minutes. The mixture was stirred at the same temperature for 1 hour, and then 3.9 l of cold water was added thereto. The organic layer was separated and washed with a mixture solution of 0 ml of a saturated sodium hydrogencarbonate aqueous solution and 3 l of water, and then with 3 l of a saturated sodium chloride aqueous solution. The organic layer was dried over anhydrous magnesium sulfate and then concentrated under reduced pressure to dryness to obtain 27 g of a crude product of p-methoxybenzyl (6R,7R)-7-(Z)-2-(2-(1-tert-butoxycarbonyl-1-methylethoxyimino)-2-(2-tritylaminothiazol-4-yl)acetamido]-3-chloromethyl-3-cephem-4-carboxylate. This crude product was used to the subsequent step without purification.

NMR(DMSO-$d_6$) δ: 1.40(15H, s), 3.60(2H, br s), 3.75(3H, s), 4.50(2H, br s), 5.08(1H, d, J=4.5 Hz), 5.12(2H, s), 5.72(1H, dd, J=4.5 and 9 Hz), 6.70(1H, s), 6.92(2H, d, J=9 Hz), 7.3(17H, m), 8.73(1H, s), 9.28(1H, d, J=9 Hz).

527 g (1.3 mol) of the crude product obtained in the above step was dissolved in 6.5 l of N,N-dimethylformamide, and 1.079 kg (6.5 mol) of potassium iodide was added thereto at a temperature of at most 5° C. The mixture was stirred for 20 minutes. To the reaction solution, 1.3 l of dimethylsulfoxide and 214.8 g (1.3 mol) of 5,6-dihydroxy-2-methylisoindoline were added, and the mixture was stirred at a temperature of from 0° to 5° C. for 3 hours. The reaction solution was added to a mixture solution of 16 l of ethyl acetate, 13 l of water and 215 ml of concentrated hydrochloric acid which were cooled to a temperature of at most 5° C. The organic layer was separated, washed with 7.8 l of water, then dried over anhydrous magnesium sulfate and concentrated under reduced pressure to dryness. The residue was dissolved in 1.6 l of methylene chloride, and 780 ml of anisole, 2.8 l of acetic acid and 780 ml of concentrated hydrochloric acid were added thereto. The mixture was stirred at room temperature for 20 hours. The reaction solution was added to 39 l of acetone cooled to a temperature of at most 5° C. under stirring, and the mixture was stirred at the same temperature for 1 hour. Precipitated insolubles were collected by filtration, washed with 4 l of acetone and then dried under reduced pressure to obtain 794 g (content determined by HPLC method: 56.7%) of the above-identified compound as powder. The yield of the product was 54.8% (which is a value already revised from the analytical value).

IR(KBr)cm$^{-1}$: 1780, 1730, 1680, 1620, 1330, 1160, 1000.

NMR(DMSO-d$_6$) δ: 1.53(6H, s), 3.08(3H, s), 3.70 and 4.12 (2H, ABq, J=18 Hz), ca. 4.8(6H, m), 5.34(1H, d, J=4.5 Hz), 5.93(b 1H, dd, J=4.5 and 9 Hz), 6.80(1H, s), 6.82(b 1H, s), 6.90(1H, s), 9.65(1H, d, J=9 Hz).

Melting point: 190° C. (decomposed).

UV(λmax): 265 nm (E$_1$ $_{cm}$$^{1\%}$ 241)(methanol).

EXAMPLE 2

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 794 g (content determined by HPLC method: 56.7%, 0.712 mol) of the hydrochloride obtained in Example 1 was dissolved in 3.9 l of methanol, and 39 g of activated carbon was added thereto. The mixture was stirred at a temperature of at most 5° C. for 1 hour. The activated carbon was removed by filtration and washed with 790 ml of methanol. Then, the filtrate and the washing solution were put together and 4.7 l of water and 1.59 l of 4N sulfuric acid were added thereto at a temperature of at most 5° C. The mixture was stirred for a short period of time to make it a homogeneous solution. The solution was left to stand at the same temperature for 1 hour and then stirred for 30 minutes. Further, 790 ml of 4N sulfuric acid was added thereto. The mixture was stirred for 30 minutes and then left to stand overnight at a temperature of at most 5° C. Precipitated crystals were collected by filtration and washed with 450 ml of a mixture solution of methanol/water (1/1) and with 450 ml of acetone. The crystals were dried in air at room temperature for 5 hours to obtain 560 g (content determined by HPLC method: 74%) of crystals of the above-identified compound. The yield of this product was 92.0% (which is a value already revised from the analytical value).

Water content (determination by weight loss on drying): 13.1%.

Content of sulfuric acid (determination by a weight method of barium chloride): 12.3%.

IR(KBr)cm$^{-1}$: 1780, 1730, 1680, 1630, 1340, 1180, 1150, 1110, 620.

NMR(DMSO-d$_6$) δ: 1.55(6H, s), 3.04(3H, s), 3.40 and 3.77(2H, ABq, J=18 Hz), ca. 4.7(6H, m), 5.25(1H, d, J=4.5 Hz), 5.88(1H, dd, J=4.5 and 9 Hz), 6.71(b 1H, s), 6.77(2H, s), 9.40(1H, d, J=9 Hz).

UV(λmax): 265 nm (E$_1$ $_{cm}$$^{1\%}$ 236) (methanol).

Melting point: 220° C. (decomposed).

EXAMPLE 3

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 2.00 g (content determined by HPLC method: 87.5%, 2.77 mmol) of the hydrate obtained in the below mentioned Reference Example 1, was suspended in 10 ml of methanol, 0.8 ml of 6N hydrochloric acid was added thereto at a temperature of at most 5° C. to dissolve the hydrate. 20 mg of activated carbon was added thereto, and the mixture was stirred at the same temperature for 30 minutes. Then, the activated carbon was removed by filtration and washed with 2 ml of methanol. The filtrate and the washing solution were put together, and 6 ml of water and 4 ml of 4N sulfuric acid were added thereto at a temperature of at most 5° C. The mixture was stirred for a short period of time to make it a homogeneous solution. This solution was left to stand at the same temperature for 5 hours. Then, crystals were collected by filtration, washed with 2 ml of a mixture solution of methanol/water (1/1) and with 2 ml of acetone and then dried in air overnight at room temperature to obtain 2.33 g (content determined by HPLC method: 73.1%) of the above-identified compound as colorless crystals. The yield of this product was 93.3% (which is a value already revised from the analytical value).

Water content (determination by weight loss on drying): 13.2%.

Content of sulfuric acid (determination by a weight method of barium chloride): 12.9%.

IR(KBr)cm$^{-1}$: 1780, 1730, 1670, 1630, 1340, 1160, 1140, 1000, 610.

NMR(DMSO-d$_6$) δ: 1.48(6H, s), 3.07(3H, s), 3.63 and 4.03 (2H, ABq, J=18 Hz), ca. 4.7(6H, m), 5.28(b 1H, d, J=4.5 Hz), 5.92(b 1H, dd, J=4.5 and 9 Hz), 6.73(1H, s), 6.77(2H, s), 9.48(1H, d, J=9 Hz).

UV(λmax): 265 nm(E$_1$ $_{cm}$$^{1\%}$ 233) (methanol).

Melting point: 220° C. (decomposed).

X-ray diffraction pattern:

The powder X-ray diffraction pattern disclosed in the following table was determined by using an X-ray having a wave length λ=1.54056–1.54435 Å (Cu: Ni X-ray) obtained by using copper as a counter cathode and a nickel filter (power source: 40 kV, 35 mA). The angles of diffraction are shown in the column identified by 2θ, the interplanar spacings are shown in the column identified by d, and the relative intensities are shown in the column identified by I/Imax.

| 2θ (°) | d (Å) | I/I max (%) |
|---|---|---|
| 7.4150 | 11.9122 | 39.94 |
| 8.0075 | 11.0321 | 44.44 |
| 8.2875 | 10.6600 | 19.14 |
| 8.8125 | 10.0261 | 33.22 |
| 9.6450 | 9.1625 | 10.65 |

-continued

| 2θ (°) | d (Å) | I/I max (%) |
| --- | --- | --- |
| 14.2450 | 6.2124 | 17.36 |
| 14.7550 | 5.9988 | 41.71 |
| 15.8275 | 5.5946 | 22.96 |
| 16.1750 | 5.4752 | 60.49 |
| 16.6925 | 5.3066 | 19.14 |
| 17.0050 | 5.2098 | 22.96 |
| 17.7025 | 5.0061 | 100.00 |
| 18.6225 | 4.7608 | 14.06 |
| 19.7075 | 4.5010 | 34.03 |
| 20.6925 | 4.2890 | 94.52 |
| 21.0200 | 4.2229 | 81.50 |
| 22.0550 | 4.0270 | 42.61 |
| 22.6575 | 3.9212 | 25.70 |
| 23.2400 | 3.8243 | 53.17 |
| 23.8875 | 3.7220 | 25.70 |
| 24.4750 | 3.6340 | 68.29 |
| 25.1800 | 3.5338 | 30.10 |
| 25.4425 | 3.4980 | 55.21 |
| 26.1350 | 3.4068 | 17.94 |
| 27.4175 | 3.2503 | 27.13 |
| 28.6150 | 3.1170 | 13.04 |
| 29.2650 | 3.0492 | 98.62 |
| 30.1750 | 2.9593 | 34.03 |
| 31.0075 | 2.8817 | 31.64 |
| 31.4950 | 2.8382 | 27.85 |
| 33.0950 | 2.7045 | 19.14 |
| 34.6500 | 2.5866 | 12.54 |
| 35.9250 | 2.4977 | 15.67 |
| 37.3200 | 2.4075 | 13.04 |
| 37.9300 | 2.3702 | 21.01 |
| 38.5975 | 2.3307 | 15.67 |
| 39.5775 | 2.2752 | 9.34 |

EXAMPLE 4

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 400 mg (content determined by HPLC method: 87.5%, 0.55 mmol) of the hydrate obtained in the below-mentioned Reference Example 1 was suspended in 2 ml of methanol and of 6N hydrochloric acid was added thereto at a temperature of at most 5° C. to dissolve the hydrate. 20 mg of activated carbon was added thereto, and the mixture was stirred at the same temperature for 30 minutes. Then, the activated carbon was removed by filtration and washed with 0.4 ml of methanol. The filtrate and the washing solution were put together, 4.8 of water and 0.8 ml of 4N sulfuric acid were added thereto at a temperature of at most 5° C. and the mixture was stirred for a short period of time to make it a homogeneous solution. This solution was left to stand overnight at the same temperature. Precipitated crystals were corrected by filtration, washed with 0.8 ml of a mixture solution of methanol/water (1/1) and with 0.8 ml of acetone and then dried in air at room temperature for hours to obtain 395 mg (content determined by HPLC method: 73.1%) of the above-identified compound as colorless crystals. The yield of this product was 82.5% (which is a value already revised from the analytical value).

Water content (determination by weight loss on drying): 13.9%.

Content of sulfuric acid (determination by a weight method of a barium chloride reagent): 11.8%.

The IR spectrum, NMR spectrum and melting point were the same as those of the compound of Example 3.

EXAMPLE 5

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 400 mg (content determined by HPLC method: 87.5%, 0.55 mmol) of the hydrate obtained in the below-mentioned Reference Example 1 was suspended in 3.2 ml of methanol, and 0.16 ml of 6N hydrochloric acid was added thereto at a temperature of at most 5° C. to dissolve the hydrate. 20 mg of activated carbon was added thereto, and the mixture was stirred at the same temperature for 30 minutes. Then, the activated carbon was removed by filtration and washed with 0.8 ml of methanol. The filtrate and the washing solution were put together, and 4.0 ml of water and 0.8 ml of 4N sulfuric acid were added thereto at a temperature of at most 5° C. The mixture was stirred for a few minutes. This solution was left to stand overnight at the same temperature. This solution was treated in the same manner as in Example 3. Then, the crystals thereby obtained was dried by blowing of dry nitrogen gas for 4 hours to obtain 380 mg of the above-identified compound as colorless crystals. The yield of this product was 84.9% (which is a value already revised from the analytical value).

Water content (determination by weight loss on drying): 9.0%.

Content of sulfuric acid (determination by a weight method of a barium chloride reagent): 12.4%.

EXAMPLE 6

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 5.00 g (content determined by HPLC method: 53.6%, 4.24 mmol) of the hydrochloride obtained in accordance with the same process as in Example 1, was dissolved in a mixture solution of 30 ml of ethanol and 30 ml of water, and 250 mg of activated carbon was added thereto at a temperature of at most 5° C. The mixture was stirred for 30 minutes. The activated carbon was removed by filtration, and 10 ml of 4N sulfuric acid was added to the filtrate. The mixture was left to stand at a temperature of at most 5° C. for 1 hour and then stirred for further 3 hours. Precipitated crystals were collected by filtration and washed with 2.5 ml of a mixture solution of ethanol/water (1/1) and with 2.5 ml of acetone. Then, the crystals were dried at room temperature by blowing of nitrogen gas for 5 hours to obtain 2.95 g of the crystals of the above-identified compound. The yield of this product was 85.6% (which is a value already revised from the analytical value).

Water content (determination by weight loss on drying): 8.7%.

Content of sulfuric acid (determination by a weight method of a barium chloride reagent): 12.3%.

EXAMPLE 7

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate The same treatment was conducted in the same manner as in Example 6 except that isopropyl alcohol was used instead of ethanol to obtain 3.22 g of the crystals of the above-identified compound. The yield of this product was 91.4% (which is a value already revised from the analytical value).

Water content (determination by weight loss on drying): 9.2%.

Content of sulfuric acid (determination by a weight method of a barium chloride reagent): 12.1%.

The IR spectrum, NMR spectrum and melting point were the same as those of the compound of the Example 3.

EXAMPLE 8

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 500 mg (content determined by HPLC method: 87.5%, 0.69 mmol) of the hydrate obtained in Reference Example 1 was suspended in a mixture solution of 5 ml of ethanol and 5 ml of water, and 0.25 ml of 6N hydrochloric acid was added thereto at a temperature of at most 5° C. to dissolve the hydrate. 25 mg of activated carbon was added thereto, and the mixture was stirred at the same temperature for 30 minutes. Then, the activated carbon was removed by filtration, and washed with 1 ml of a mixture solution of ethanol/water (1/1). The filtrate and the washing solution were put together, and 1 ml of 4N sulfuric acid was added thereto at a temperature of at most 5° C. The mixture was left to stand overnight at the same temperature. Hereinafter, the filtration and the washing were conducted in the same manner as in Example 6, and then the crystals thereby obtained was dried in vacuum at room temperature for 2 hours to obtain 450 mg of the above-identified compound as colorless crystals. The yield of this product was 84.7% (which is a value already revised from the analytical value).

Water content (determination by weight loss on drying): 2.6%.

Content of sulfuric acid (determination by a weight method of a barium chloride reagent): 12.7%.

UV(λmax): 266($E_1\ cm^{1\%}$ 261) (methanol).

EXAMPLE 9

(6R,7R)-7-[(Z) 2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate 2.87 g (content determined by HPLC method: 67.3%, 3.05 mmol) of the sulfate obtained by the same operation as in Example 2 was suspended in 14.4 ml of methanol, and 1.44 ml of concentrated hydrochloric acid was added thereto at a temperature of at most 5° C. to dissolve the sulfate. 30 mg of activated carbon was added thereto, and the mixture was stirred at the same temperature for 1 hour. Then, the activated carbon was removed by filtration and washed with 2.9 ml of methanol. The filtrate and the washing solution were put together, and 17.3 ml of water and 5.7 ml of 4N sulfuric acid were added thereto at a temperature of at most 5° C. The mixture was left to stand for 2 hours and then stirred for 1 hour. Precipitated crystals were collected by filtration, washed twice with 3 ml of a mixture solution of methanol/water (1/1) and twice with 2 ml of acetone and then dried in vacuum at room temperature for 2 hours to obtain 2.16 g of the above identified compound as colorless crystals. The yield of this product was 94.0% (which is a value already revised from the analytical value).

Water content (determination by weight loss on drying): 2.5%.

Content of sulfuric acid (determination by a weight method of a barium chloride reagent): 13.2%.

REFERENCE EXAMPLE 1

(6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate hydrate 35.5 g (content determined by HPLC method: 56.2%, 31.5 mmol) of the hydrochloride obtained by the same operation as in Example 1 was suspended in 300 ml of water, 1N caustic soda was added thereto under cooling with ice until pH became 3.5, and 8.9 g of sodium sulfite was added thereto. Further, 1N caustic soda was added thereto for dissolution until pH became 6.3, and insolubles were removed by filtration. The filtrate was subjected to reversed phase column chromatography (ODS, 380 ml) and eluted with water and 10% methanol. About 1.7 l of the fractions containing the desired compound was put together and concentrated under reduced pressure to about 500 ml. 8.4 ml of trifluoroacetic acid was added to the concentrate under cooling with ice. This solution was subjected to reversed phase column chromatography (ODS, 380 ml) and eluted with water, a 1.5% tetrahydrofuran aqueous solution and a 2.5% tetrahydrofuran aqueous solution. About 5 l of the fraction containing the desired product was put together and concentrated under reduced pressure until insolubles started to precipitate. Seed crystals of the hydrate were added thereto, and the mixture was left to stand at room temperature for 40 minutes. Further, the mixture was concentrated under reduced pressure to an amount of about 80 ml and left to stand overnight at 5° C. Precipitated crystals were collected by filtration, washed with 10 ml of cold water, with 10 ml of ethanol and with 10 ml of acetone, and then dried in air at room temperature for 5 hours to obtain 15.0 g of the above-identified compound as colorless crystals. The yield of this product was 65.7% (which is a value already revised from the analytical value).

IR(KBr)cm$^{-1}$: 1780, 1730, 1680, 1620, 1540, 1470, 1400, 1340, 1160.

NMR(D$_2$O, NaHCO$_3$) δ: 1.52(6H, s), 3.15(3H, s), 3.43 and 3.80(2H, ABq, J=18 Hz), ca. 4.6(6H, m), 5.25(1H, d, J=4.5 Hz), 5.72(1H, d, J=4.5 Hz), 6.78(1H, s), 6.83 (2H, s).

UV(λmax): 264 nm($E_1\ cm^{1\%}$ 266) (methanol).

INDUSTRIAL APPLICABILITY

The stable crystalline (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate which is a useful compound as a medicine for curing infectious diseases caused by bacteria is provided by the present invention. Therefore, the present invention substantially contributes to the reduction of cost for the production of the compound and in the use as the medicine for curing infectious diseases caused by bacteria.

We claim:

1. Crystalline (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate.

2. A process for producing a compound of claim 1, wherein an acid addition salt of (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate, its hydrate, solvate or non-crystalline powder, or a crude product thereof is added to water, a hydrophilic organic solvent or a mixture thereof, and then, sulfuric acid and, if necessary, water are added thereto to precipitate crystals of (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate.

3. The process for producing a compound according to claim 2, wherein (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate hydrochloride or its hydrate is added to water, a hydrophilic organic solvent or a mixture thereof, and then, sulfuric acid and, if necessary, water are added thereto to precipitate crystals of (6R,7R)-7-[(Z)-2-(2-aminothiazol-4-yl)-2-(1-carboxy-1-methylethoxyimino)acetamido]-3-(5,6-dihydroxy-2-methyl-2-isoindolinium)methyl-3-cephem-4-carboxylate sulfate or its hydrate.

* * * * *